US009244030B2

(12) United States Patent
Vokey et al.

(10) Patent No.: US 9,244,030 B2
(45) Date of Patent: Jan. 26, 2016

(54) METHOD OF DETECTING A LEAK IN A MEMBRANE OF A ROOF

(71) Applicant: Detec Systems LLC, Tacoma, WA (US)

(72) Inventors: David E. Vokey, Sidney (CA); Walter Isaac Jordan, Blaine, WA (US)

(73) Assignee: Detec Systems LLC, Bellingham, WA (US)

( * ) Notice: Subject to any disclaimer, the term of this patent is extended or adjusted under 35 U.S.C. 154(b) by 301 days.

(21) Appl. No.: 13/939,698

(22) Filed: Jul. 11, 2013

(65) Prior Publication Data

US 2014/0361796 A1 Dec. 11, 2014

(30) Foreign Application Priority Data

Jun. 6, 2013 (CA) .................................... 2818121

(51) Int. Cl.
*G01N 27/04* (2006.01)
*G01N 27/20* (2006.01)
*G01M 3/40* (2006.01)

(52) U.S. Cl.
CPC ................ *G01N 27/04* (2013.01); *G01M 3/40* (2013.01); *G01N 27/20* (2013.01)

(58) Field of Classification Search
CPC .................................................. G01N 27/04
USPC ................................................ 324/693, 705
See application file for complete search history.

(56) References Cited

U.S. PATENT DOCUMENTS

| 7,924,031 | B2* | 4/2011 | Watkins et al. | 324/693 |
| 2007/0046481 | A1* | 3/2007 | Vokey et al. | 340/602 |
| 2009/0091337 | A1* | 4/2009 | Robinson et al. | 324/693 |
| 2010/0141283 | A1* | 6/2010 | Vokey | 324/705 |
| 2011/0089958 | A1* | 4/2011 | Malecki et al. | 324/693 |

FOREIGN PATENT DOCUMENTS

WO 2009023956 2/2009

* cited by examiner

*Primary Examiner* — Arleen M Vazquez
*Assistant Examiner* — Brent J Andrews
(74) *Attorney, Agent, or Firm* — Adrian D. Battison; Ade & Company Inc

(57) ABSTRACT

In a method of detecting a leak in a water impermeable membrane applied on a roof substrate, an electrical potential is created between a conductive detector on top of the membrane and the roof substrate causing current to flow between the roof substrate and the conductive detector through moisture in any leak in the membrane. The membrane is attached to the roof support substrate by an intervening layer therebetween which can be a primer or an adhesive layer which is caused to be electrically conductive by the addition an electrically conductive material. This allows the conductor on the roof substrate to which the potential difference is applied to be attached onto the roof substrate and covered by the layer underneath the membrane.

17 Claims, 1 Drawing Sheet

METHOD OF DETECTING A LEAK IN A MEMBRANE OF A ROOF

This invention relates to a method of detecting a leak in a water impermeable membrane of a roof using low voltage to generate a current through any defects which can be detected by sensors on top of the membrane.

BACKGROUND OF THE INVENTION

The failure to detect, find and correct membrane defects during and as soon after its installation as possible, can cause premature failure. Problems include design deficiencies, faulty application of the membrane system and damage by subsequent tradesmen. Roof designs incorporating a waterproofing membrane under a green roof, insulation layer, wear-course, or topping slab greatly exacerbate the problem of leak locating. The early detection of leaks in waterproof membranes is crucial during construction and for effective roof maintenance. Leaks in conventional roof assemblies allow moisture to accumulate under the membrane in the underlying components such as protection boards and insulation. Accumulated water in insulation compromises its thermal properties. Accumulated water in construction materials can cause rotting and other damage which is very costly to repair.

Low voltage electrical conductance testing is often used to detect and locate leaks in waterproof membranes. The principle technique of the conductance leak location method is to establish an electrical potential between the electrically insulating membrane and the underlying roof substrate. A controlled surface covering of water forms the conductive path horizontally across the membrane to any membrane breach. At a breach location, the test instrument detects the electrical path that is formed through the water leaking to the conductive substrate below.

Low voltage electrical methods to detect and locate breaches are highly effective; however they require an electrically conductive surface immediately below and in intimate contact with the membrane. Often membranes in conventional assemblies are adhered or mechanically fastened to non-conductive materials such as plywood substrate or protection boards which inhibit electric conductance testing.

SUMMARY OF THE INVENTION

According to one aspect of the invention there is provided a method of detecting a leak in a water impermeable membrane comprising:

applying a water impermeable membrane onto a generally horizontal roof support substrate;

generating an electrical potential between a conductive detector on top of the membrane and the non-conductive roof sub such that current will flow between the roof substrate and the conductive detector through moisture in any leak located within the zone;

sensing the current between the roof substrate and the conductive detector so as to detect any leak;

the membrane being attached to the roof support substrate by an intervening layer therebetween;

wherein the intervening layer includes electrically conductive material.

Preferably the intervening layer contains an adhesive material so as to bond the membrane to the roof substrate.

However the intervening layer can comprise a primer which is then optionally covered by an adhesive layer of a conventional nature.

Preferably the intervening layer comprises a base material that is chemically compatible with the membrane and a conductive filler material to provide the required conductivity.

The primer or layer can be applied directly to a structural component of the roof so that the substrate to which it is applied is the structural component such as the concrete deck of the roof. Alternatively the primer or layer can be applied to an additional cover-board, which is placed over the assembly as a protective layer, where the primer lies on the cover board directly under the membrane. Thus the primer coats the surface of the board with a conductive material as described above. The cover board may typically be an asphaltic or treated gypsum-core panel protection board, but other materials maybe used.

Preferably the intervening layer has a resistance level in the range $1 \times 10^2$ to $1 \times 10^7$ ohms per square. This can be obtained by providing a loading of the conductive filler which lies in the range from four to thirty percent (4% to 30%). This level of resistance provides a conductivity which is very low in comparison with other materials since the current flow can be detected at very low levels. This loading of the filler can be achieved without interfering with the other properties of the carrier material and at relatively low cost.

Preferably the electric potential at the roof substrate is provided by a conductor in electrical connection with the intervening layer. In this way there is no requirement to connect the potential difference to roof substrate itself. Thus the conductor can be applied onto the roof substrate as a metal plate of an elongate conductor and covered with the intervening layer.

Preferably the leak detection is carried out by sensing the current between the roof substrate and the conductive detector using a conductor applied on top of the membrane which is connected to the low voltage potential difference and includes a sensor in the circuit to detect the current that is created through the membrane by the leak. The detection methods can be of the type described in PCT Publication WO 2009/023956 of the present Applicant and present inventor published 26 Feb. 2009, the disclosure of which is incorporated by reference.

Thus the method includes for example arrangements where the conductor applied on top of the membrane is a movable probe or is an array of fixed conductive wires. However other sensing systems may be used Also it should be noted that the conductive primer could be placed under a loose laid membrane, that is with no adhesives used. The main idea is to get a conductive easily applied (paintable) conductive layer between the membrane and the non-conductive substrate.

The present invention overcomes the above limitations while providing a conductive ground plane for conductance testing of waterproof membranes.

While a conductive ground plane under a waterproof membrane is required for conductance testing the resistivity of the ground plane can be reasonably high while still providing and adequate return path for the testing currents. A return path of several thousand ohms provides an adequate return path for conductance testing instruments which can detect breach paths ranging in the hundreds of thousands of ohms. To that end, a ground plane with sufficient conductivity for conductance testing can be applied as a conductive primer to the substrate surface. The primer is composed of a liquid base material that is chemically compatible with the membrane being used. A conductive filler is added such as carbon or steel fibers, carbon black, carbon nanotubes (CNTs) or graphite. Adequate conductance can be achieved with loadings from two to seven percent depending on the material selected. The loaded primer is then rolled over the substrate surface to provide a continuous grounding layer. At vertical interfaces such as parapets or walls the conductive primer can be rolled up the surface to allow testing of the waterproof membrane when applied on vertical surfaces. Electrical connection to the conductive primer can be accomplished by securing a metal plate with a ground wire lead to the roof substrate and brushing or rolling the primer over it to establish a connection to the rest of the primed substrate. A second method to ensure a good and continuous connection to the conductive primer is to adhere long conductive copper strips to the roof substrate prior to applying the primer.

In a second embodiment the membrane is fully adhered to the substrate using an adhesive with conductive filler which would then provide the testing ground plane as described above.

BRIEF DESCRIPTION OF THE DRAWINGS

One embodiment of the invention will now be described in conjunction with the accompanying drawings in which.

DETAILED DESCRIPTION

In the method shown in the Figures there is provided a water impermeable membrane 10 applied onto a generally horizontal roof support substrate 11.

Figure 1:
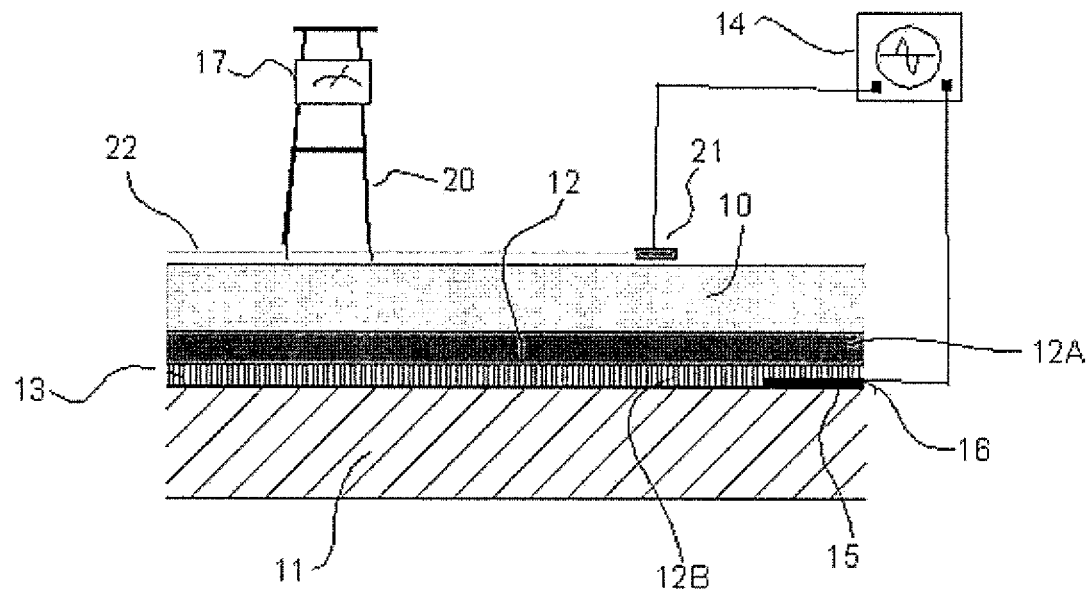
FIG. 1 is a cross-sectional view through a roof substrate and membrane showing a first method of detecting leaks or defects in the membrane according to the present invention

The membrane 10 is applied to the roof substrate by an intervening layer 12 therebetween where the intervening layer 12 includes electrically conductive material 13. In FIG. 1, the intervening layer includes a primer layer 12A and an adhesive layer 12B where the adhesive layer contains an adhesive material. The intervening layer 12 thus comprises an adhesive material that is chemically compatible with the membrane 10 together with the conductive filler material 13 to render the layer immediately on top of the substrate electrically conductive.

An electric potential at the roof substrate is provided by a conductor 15 in electrical connection with the intervening layer 12B and connected to one terminal of a generator 14. The conductor 15 in FIG. 1 comprises a metal plate 16 applied onto and attached to the roof substrate and covered with the intervening layer 12.

In In the method an electrical potential is applied from the generator 14 between a conductor 21 on top of the membrane 10 and the layer 12B such a current will flow from surface conductor 21 through water sprayed on the membrane surface 22 through any moisture leak in the membrane, to the conductive layer 12B and the returned to the generator through grounding conductor 16.

In a second embodiment, the grounding conductor 16 can be an copper wire or flat conductor to provide continuous grounding of the conductive material 13 along the length and width of the roof substrate.

The current between the roof substrate and the conductive detector is sensed by a conductor probes 20 applied on top of the membrane and by a sensing circuit 17 attached to the conductor probes 20. The details of such arrangements are shown in the above identified PCT publication.

Figure 2:
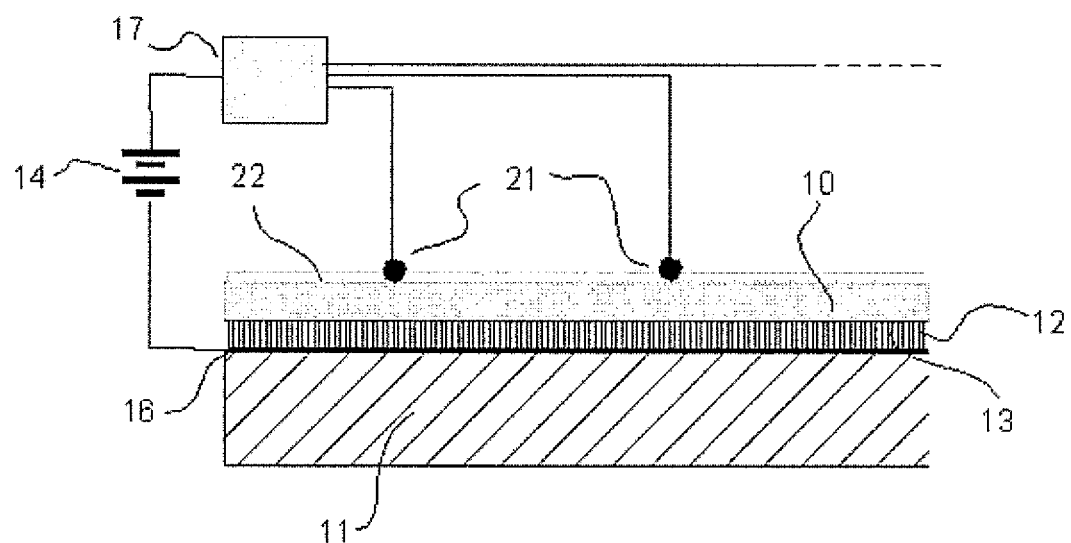
FIG. 2 is a cross-sectional view similar to FIG. 1 showing a second modified method according to the present invention In the drawings like characters of reference indicate corresponding parts in the different figures.

In FIG. 2, the layer 12 comprises wholly an adhesive layer containing the conductive material 13. In this embodiment the conductor 16 comprises an elongate tape where the conductor sits on a self-adhesive substrate adhered to the roof substrate and covered by the layer 12.

In this embodiment, the sensing circuit 17 is attached to an array of fixed conductors 21 which operate in the manner set out in the above publication.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of detecting a leak in a water impermeable membrane comprising:
    applying a water impermeable membrane onto a generally horizontal non-conducting roof substrate;
    an undersurface of the membrane being adhesively attached to the roof support substrate by an intervening layer covering the undersurface located between the undersurface and the roof support substrate;
    wherein the intervening layer includes an electrically conductive material;
    generating an electrical potential between a conductive detector on top of the membrane and the intervening layer by a conductor in electrical connection with the intervening layer such that current will flow between the intervening layer and the conductive detector through moisture in any leak in the membrane;
    and sensing the current between the intervening layer and the conductive detector so as to detect any leak.

2. The method according to claim 1 wherein the intervening layer contains an adhesive material.

3. The method according to claim 1 wherein the intervening layer comprises a primer.

4. The method according to claim 1 wherein the electrically conductive material comprises a conductive filler material.

5. The method according to claim 4 wherein the conductive filler material comprises conductive fibers such as carbon or steel fibers.

6. The method according to claim 4 wherein the conductive filler material comprises carbon black.

7. The method according to claim 4 wherein the conductive filler material comprises carbon nanotubes (CNTs).

8. The method according to claim 4 wherein the conductive filler material comprises graphite.

9. The method according to claim 4 wherein the loading of the conductive filler material lies in the range from 4% to 30%.

10. The method according to claim 1 wherein the intervening layer has a resistance level in the range $1 \times 10^2$ to $1 \times 10^7$ ohms per square.

11. The method according to claim 1 wherein said conductor is applied onto the roof substrate and covered with the intervening layer.

12. The method according to claim 1 wherein said conductor is a metal plate.

13. The method according to claim 1 wherein said conductor is an elongate conductive strip.

14. The method according to claim 13 wherein said elongate conductive strip is carried on a non-conductive substrate which is adhesively attached to the roof substrate.

15. The method according to claim 1 wherein the current between the roof substrate and the conductive detector is sensed by a conductor applied on top of the membrane.

16. The method according to claim 15 wherein the conductor applied on top of the membrane is a movable probe.

17. The method according to claim 15 wherein the conductor applied on top of the membrane is an array of fixed conductive wires.

* * * * *